United States Patent [19] … [11] 4,258,179
Kawata et al. … [45] Mar. 24, 1981

[54] COATING AGENTS FOR SOLID MEDICAMENTS

[75] Inventors: Hiroitsu Kawata, Kawagoe; Tadayoshi Ohmura, Niiza; Hiroyoshi Shiozawa, Tokyo; Munetaka Hattori, Yaizu, all of Japan

[73] Assignee: Yamanouchi Pharmaceutical Co., Ltd., Tokyo, Japan

[21] Appl. No.: 971,498

[22] Filed: Dec. 20, 1978

[30] Foreign Application Priority Data

Dec. 29, 1977 [JP] Japan ................ 52-158102

[51] Int. Cl.$^3$ ............... B01J 13/00; C08B 11/08
[52] U.S. Cl. ................ 536/95; 106/170; 106/197 R; 106/203; 241/28; 252/316; 427/3; 428/407
[58] Field of Search ............. 428/542; 424/35; 536/87, 95; 106/170, 197 R, 203; 241/28; 428/542, 407; 427/3; 252/316

[56] References Cited

U.S. PATENT DOCUMENTS

| | | | |
|---|---|---|---|
| 2,565,420 | 8/1951 | Ayers | 241/28 |
| 3,493,407 | 2/1970 | Greminger et al. | 106/170 |
| 3,640,741 | 2/1972 | Etes | 106/170 |
| 3,798,054 | 3/1974 | Kawata et al. | 424/35 |
| 3,852,421 | 12/1974 | Koyanagi et al. | 424/361 |
| 3,899,439 | 8/1975 | Mahlman | 106/197 R |
| 4,076,935 | 2/1978 | Eichenseer et al. | 241/28 |
| 4,091,205 | 5/1978 | Onda et al. | 536/95 |
| 4,097,667 | 6/1978 | Holst et al. | 106/170 |

OTHER PUBLICATIONS

Chemical Abstracts, vol. 85 (1976), p. 25400y.
Chemical Abstracts, vol. 75 (1971), p. 40461f.

Primary Examiner—Ronald W. Griffin
Attorney, Agent, or Firm—Burgess, Ryan and Wayne

[57] ABSTRACT

A novel coating agent for solid medicaments containing a hydrogel-like substance of a water-insoluble hydroxypropyl cellulose having 5–16% by weight of a hydroxypropoxy group or the dry powder of a hydrogel-like substance. By coating solid medicaments with the coating agent, solid medicaments having high impact resistance and showing very less aging can be provided advantageously in industry.

20 Claims, No Drawings

COATING AGENTS FOR SOLID MEDICAMENTS

BACKGROUND OF THE INVENTION

1. Field of the Invention

The present invention relates to a novel coating agent for solid medicaments such as tablets, pills, granules, fine granules, etc. More particularly, the invention relates to a novel coating agent for solid medicaments containing a hydrogel-like substance of a water-insoluble hydroxypropyl cellulose having 5-16% by weight of a hydroxypropoxy group or the dry powder of a hydrogel-like substance. The invention relates further to a method of coating solid medicaments with the coating agent, the solid medicaments coated with the coating agent, and a method of producing the hydrogel-like substance or the dry powder thereof.

2. Description of the Prior Art

As coating agents for solid medicaments which have generally been used, there are a sugar coating agent containing sugar and a film coating agent containing a high molecular compound (without containing sugar). The coating agent which has been most frequently used is a sugar coating agent and in general, binding agent(s) is compounded therein for keeping the intensity of the sugar coated layer. However, conventional binding agents have various problems from various view points. For example, when gelatin which is frequently used as a binding agent at present is used, aging, that is, a discoloring phenomenon (e.g., a brown coloring phenomenon) occurs with the passage of time to reduce the commercial value of the product and further, the sugar coated layer becomes insoluble with the passage of time to cause the possibility of prolonging the disintegration time (disintegration delay) of the sugar coated layer. They are considered to be based on the denaturation of the protein of gelatin. When gum arabic is used as a binding agent, the binding strength is insufficient and hence the sugar coated layer is liable to cause cracking or breakage by impact, etc., (i.e., lacking in impact resistance). Recently, it has been attempted to use polyvinylpyrrolidone, polyvinyl alcohol, water-soluble cellulose ether derivatives, α-starch, etc., as binding agents but even if these binding agents are used, there still remain various problems that the suspending property and viscosity of the sugar coating agent are unsuitable for coating and the binding strength is insufficient.

Hitherto, as a method of coating solid medicaments with a coating agent, there are generally employed a pouring method and a spray method. However, it is practically difficult to form a sugar coating by the spray method using a sugar coating agent. That is, conventional sugar coating agents have problems in the adhesive property and growing property of the agents as well as the strength and the appearance of the coated solid medicaments and hence they are unsuitable for use in a spray coating method.

SUMMARY OF THE INVENTION

As the result of various investigations under such technical level, the inventors have discovered that by grinding or kneading a water-insoluble hydroxypropyl cellulose containing 5-16% by weight of a hydroxypropoxy group (hereinafter, the hydroxypropyl cellulose is referred to as HPC-US) in the presence of water, a hydrogel-like substance (hereinafter, referred to as hydrogel-like HPC-US) is obtained and the coating agents for solid medicaments containing the hydrogel-like substance or the dry powder thereof are very useful.

That is, according to this invention, there is provided a novel sugar coating agent for solid medicaments containing hydrogel-like HPC-US or the dry powder thereof.

DESCRIPTION OF THE PREFERRED EMBODIMENTS

The hydrogel-like HPC-US or the dry powder thereof used in this invention possesses various properties required as a binding agent for sugar coating. That is, the solid medicaments coated with the sugar coating agent containing the hydrogel-like HPC-US or the dry powder thereof have excellent impact resistance since the strength of the sugar coated layer is sufficiently kept and scarcely show aging, that is, occurrence of discoloring (for example, brown coloring) with the passage of time, the delay of disintegration time, and the formation of cracking of the sugar coated layer caused by the expansion of the layer by the generation of gas, moisture absorption, etc. Furthermore, in case of coating with the sugar coating agent, the amount of the sugar coating agent to be used may be less and the time required for coating may be shorter than those in conventional sugar coating methods, which make it possible to simplify the coating process and reduce the cost for coating. Thus, the use of the sugar coating agent of this invention is very advantageous for industrial practice. Also, the sugar coating agent of this invention can be used not only in a coating method by pouring but also in a spray coating method which has been considered to be inapplicable in practical use in case of using a conventional sugar coating agent. Further, the solid medicaments coated with the sugar coating agent by the spray coating method have also excellent properties as described above. In addition, the solid medicaments coated using the dry powder of the hydrogel-like HPC-US as a dusting powder of the type usually used at sugar coating have also excellent properties as above.

Moreover, the hydrogel-like HPC-US or the dry powder thereof possesses various properties required as film coating agents. That is, the solid medicaments coated by the film coating agent containing the hydrogel-like HPC-US or the dry powder thereof have good appearance and strength and show less swelling by moisture absorption as compared with the solid medicaments coated by a conventional film coating agent. Also, since HPC-US itself is inexpensive as compared with high molecular compounds usually used for conventional film coating and the film coating agent of this invention involves the use of water without using any organic solvent, solid medicaments film-coated can be provided advantageously for industrial practice.

The above-mentioned merits of the coating agent for solid medicaments containing the hydrogel-like HPC-US or the dry powder thereof are based on the very specific properties of the hydrogel-like HPC-US or the dry powder thereof.

HPC-US used in this invention is the cellulose in which a part of the hydroxyl groups existing in the glucose residue of the cellulose have been replaced with hydroxypropoxy groups and is same as the hydroxypropyl cellulose prescribed by the Japanese Pharmacopoeia in the fundamental structure but differs from the latter in the following points. That is, while the hydroxypropyl cellulose by the Japanese Pharmacopoeia (hereinafter, the hydroxypropyl cellulose is referred to as HPC) has a hydroxypropoxy group content of 53–78% and is soluble in water, HPC-US has a low hydroxypropoxy group content of 5–16% and is scarcely soluble in water.

HPC-US is commercially available as the trade name of, for example, L-HPC (made by Shinetsu Kagaku Kogyo K.K.) and is mainly used as an excipient for pharmaceutical formulations as disclosed in, for example, U.S. Pat. No. 3,852,421. HPC-US is a white to white gray fibrous crystal or powder having almost no taste and odor. The inventors have first succeeded in obtaining good results by making the hydrogel-like substance from HPC-US and incorporating the hydrogel-like substance in a coating agent for solid medicaments.

The hydrogel-like HPC-US used in this invention is prepared by grinding or kneading 1 part by weight of HPC-US in the presence of 5–20 parts, preferably 7–13 parts of water. The grinding or kneading is effected by means of mortar and pestle, colloid mill, hammer mill, Manton-Gaulin (Gaulin homogenizer), etc. For example, where a mortar and pestle is used, it is preferred to grind or knead HPC-US while adding water in several steps. Practically, it is preferred that 1–2 parts of water is added to 1 part of HPC-US followed by grinding or kneading, then 1–2 parts of water is added thereto followed by grinding or kneading, and this procedure is repeated several times. Also, in case of using a colloid mill, sample mill, Manton-Gaulin, etc., it is preferred to suspend 1 part of HPC-US in 5–20 parts of water and then grind or knead the suspension.

The dry powder of the hydrogel-like HPC-US is produced by drying the hydrogel-like HPC-US thus prepared by spray drying, lyophilization, etc.

The hydrogel-like HPC-US prepared as described above is a viscous gel-like substance and posseses a very high viscosity as well as excellent dispersibility and suspending property as compared with those of simple suspension of HPC-US in water without being ground or kneaded. Also, when a simple suspension of HPC-US in water without being ground or kneaded is dried, HPC-US returns almost to the original powdery state but when hydrogel-like HPC-US is dried in the state of plate of 2–5 mm thick, a solid plate-like mass which is not broken by hands is formed and when hydrogel-like HPC-US is dried in thin layer, a transparent or translucent film is obtained. Furthermore, the dry powder of the hydrogel-like HPC-US has a very peculiar property in that the powder becomes the original gel-like substance again only by adding thereto water.

The coating agent of this invention is used for coating solid medicaments such as tablets, pills, granules, fine granules, etc.

The coating agent of this invention is in a liquid state or a powdery state. In the case of the liquid coating agent, the hydrogel-like HPC-US or the dry powder thereof is used and the compounding ratio thereof is 0.1–30% by weight as HPC-US. Practical examples of the liquid coating agent are a sugar coating solution and a film coating solution. In the case of the powdery coating agent, the dry powder of the hydrogel-like HPC-US is used and the compounding ratio thereof is 5–100% by weight. Practical example of the powdery coating agent is a dusting powder at sugar coating.

Then, the manner of using the coating agent of this invention will be explained below in detail.

A. Use for sugar coating:

Sugar coating of solid medicaments with the coating agent of this invention is practiced by a pouring method or a spray coating method.

(a) In the pouring method, the compounding ratio of the hydrogel-like HPC-US or the dry powder thereof added to a sugar coating solution is 0.1–15% by weight, preferably 1–10% by weight as HPC-US.

There is no particular limitation about the compounding ratio of sucrose but it is usually 5–70% by weight, preferably 50–65% by weight. The application of sugar coating onto solid medicaments by the pouring method is performed by a conventional manner using a coating pan.

Also, the powdery coating agent of this invention is frequently used as a dusting powder usually used for sugar coating by a pouring method and in this case, the compounding ratio of the dry powder of hydrogel-like HPC-US is 5–100% by weight.

Also, the hydrogel like HPC-US or the dry powder thereof of this invention may be used in the sugar coating method using calcium lactate developed previously by the same inventors (see, U.S. Pat. No. 3,798,054) and the compounding ratio of the hydrogel-like HPC-US or the dry powder thereof is 1–10% by weight as HPC-US, and that of calcium lactate is 1–20% by weight.

These sugar coating solutions and dusting powders used for the pouring method may further contain other ingredients, for example, a masking agent, an expander, a coloring agent, a sweetening agent, etc., such as titanium dioxide, calcium sulfate, calcium carbonate, lake pigment, sorbit, etc.

(b) In the spray coating method, the compounding ratio of the hydrogel-like HPC-US or the dry powder thereof added to the sugar coating solution is 0.1–10% by weight, preferably 3–7% by weight as HPC-US. There is no particular limitation about the compounding ratio of sucrose but it is usually 5–50% by weight, preferably 10–30% by weight. The application of sugar coating onto a solid medicaments by a spray coating method may be performed by spraying the sugar coating solution using a coating pan or a method using a fluidized-bed coating apparatus. Also, the above-mentioned sugar coating agent using calcium lactate to which the hydrogel-like HPC-US or the dry powder thereof is added can be used in the spray coating method. In this case, the preferred compounding ratio of the hydrogel-like HPC-US or the dry powder thereof is 3–7% by weight as HPC-US and that of calcium lactate is 3–15% by weight.

The sugar coating agent for spray coating method may further contain other ingredients such as a masking agent, an expander, a coloring agent, a sweetening agent, etc., as in the case of using a pouring method.

B. Use for film coating:

In the case of flim-coating solid medicaments with the coating agent of this invention, the coating procedure is performed by a pouring method or a spray coating method as in the case of sugar coating. The coating agent of this invention may be usually used for film coating using water but as a matter of course, an organic solvent may also be used. In this case, the compounding ratio of the hydrogel-like HPC-US or the dry powder thereof added to the film coating agent is 1–10% by weight. In this case, it is preferred to use a high molecular compound usually added to a film coating agent, such as hydroxypropylmethyl cellulose, hydroxypropyl cellulose, etc., together with the hydrogel-like HPC-US or in the form of the dry powder.

Examples of producing hydrogel-like HPC-US and the dry powder thereof:

(a) To 1 part by weight of HPC-US is added 1 part of water, the mixture is ground for 15 minutes by means of a mortar and pestle, then 1 part of water is added to the mixture followed by grinding for 15 minutes, and the same procedure is repeated 8 times to provide the viscous hydrogel-like HPC-US. Also, by drying the hydrogel-like HPC-US by spray drying, the dry powder of the hydrogel-like HPC-US is obtained.

(b) To 9 parts by weight of water is added 1 part of HPC-US and the suspension is passed through a hammer mill (1 mm screen) to provide a viscous hydrogel-like HPC-US. By drying the hydrogel-like HPC-US by means of spray drying, the dry powder of the hydrogel-like HPC-US is obtained.

In thermogravimetry, the decomposition starting temperature of the dry powder of the hydrogel-like HPC-US is about 15° C. higher than untreated HPC-US. In X-ray powder diffraction, the powder of the hydrogel-like HPC-US shows the same diffraction curve at d=4.44 Å but its full width of half maximum (FWHM) is smaller as compared with untreated HPC-US. From the polarizing microphotograph, it is observed that the crystalline property of the powder of the hydrogel-like HPC-US is different as having more amorphous portion from untreated HPC-US. Further, it is observed from electron microphotographs that untreated HPC-US is a fibrous crystal but the dry powder of hydrogel-like HPC-US does not show a fibrous appearance but shows a fused substance-like appearance. From these observations, it is clear that the powder of the hydrogel-like HPC-US has different physical and chemical properties from untreated HPC-US.

As compared with a simple suspension of untreated HPC-US in water, the hydrogel-like HPC-US has a paste-like appearance a high viscosity and excellent dispersibility and suspending properties.

Now, the experimental result made for comparing viscosity is shown below.

Experimental procedure: the viscosity of a simple suspension of untreated HPC-US in water at a concentration of 7% and the viscosity of the hydrogel-like HPC-US at the same concentration were measured for 10 seconds at 23° C. and rotor No. 2 using B-type viscometer [Vismetron (made by Shibaura System K.K.)]. The results are shown in Table 1.

TABLE 1

| Rotation rate of rotor Test sample | 6 r.p.m. | 12 r.p.m. | 30 r.p.m. | 60 r.p.m. |
|---|---|---|---|---|
| Hydrogel-like HPC-US | 2,000 cps | 1,350 cps | 850 cps | 500 cps |
| Aqueous suspension of untreated HPC-US | 100 cps | 50 cps | 25 cps | 20 cps |

Also, when the simple suspension of untreated HPC-US was dried, the suspension almost returned to the state of the original powder (untreated HPC-US) but when the hydrogel-like HPC-US of this invention was dried to a thickness of 2-5 mm, a solid plate-like mass which could not be manually broken formed and when it was dried as a thin layer, a transparent or translucent film formed. Also, the dry powder of hydrogel-like HPC-US obtained by spray drying returned again to the original hydrogel-like HPC-US by only adding water thereto.

EXAMPLE 1

(Sugar Coating)

(1) A sugar coating agent was prepared in the following formulation.

| Hydrogel-like HPC-US*[1] | 3 parts (as HPC-US) |
|---|---|
| Sucrose | 58 parts |
| Calcium lactate | 4 parts |
| Talc | 5 parts |
| Water | 30 parts |

*[1]: Prepared using L-HPC made by Shinetsu Kagaku Kogyo K. K.

A mixture of 3 parts of untreated HPC-US and the same amount of water was ground for 15 minutes by means of mortar and pestle and then after further adding thereto the same amount of water, the mixture was ground for 15 minutes. Then, while further adding slowly remaining water, the mixture was further ground for 30 minutes to provide a hydrogel-like HPC-US. By dissolving or suspending the product together with other additives, the sugar coating agent was prepared.

(2) Sugar coated tablets were prepared using the above-described sugar coating agent and the following test was performed.

Preparation of sugar coated tablets:

In a coating pan was charged core tablets of 120 mg/tablet and the core tablets were coated with the above-described sugar coating agent using an ordinary sugar coating method by pouring until the weight of the tablet became 180 mg/tablet.

In addition, as a control test, core tablets were similarly coated using a sugar coating agent prepared using HPC-US itself in place of the hydrogel-like HPC-US in the above formulation.

Impact test:

In a centrifuge tube of 50 ml, were placed 30 tablets and after shaking for a definite period of time in horizontal direction at an amplitude of 4 cm and a shaking speed of 328 reciprocation, the formation of peeled fragments of the sugar coated layer were inspected. The results are shown in Table 2.

TABLE 2

| Occured number of peeled fragments of coated layer: | | |
|---|---|---|
| | Shaking time (min.) | |
| Test sample | 3 min. | 10 min. |
| Sugar coated tablets of the invention | 0/30 | 5/30 |
| Control | 7/30 | 25/30 |

EXAMPLE 2

(Sugar Coating)

(1) A sugar coating agent was prepared in the following formulation as in Example 1.

| Hydrogel-like HPS-US*[1] | 1.5 parts (as HPC-US) |
|---|---|
| Sucrose | 65 parts |
| Water | 33.5 parts |

(2) Sugar coated tablets were prepared using the above-described sugar coating agent by a pouring method as in Example 1 and then the following test was performed. In addition, as a control, sugar coated tablets were also prepared similarly using a sugar coating agent prepared by employing 1.5 parts of gelatin in place of hydrogel-like HPC-US in the above-mentioned formulation and the same test was performed.

Impact test:

The same test as in Example 1 was performed and the following results are obtained.

TABLE 3

Occured number of peeled fragments of sugar coated layer:

| Test sample | Shaking time 3 min. |
|---|---|
| Sugar coated tablets of the invention | 3/30 |
| Control | 30/30 |

Heat resisting test:

The sugar coated tablets were subjected to a heat resisting test for 2 months at 60° C. and the following results are obtained.

TABLE 4

| Test sample | Brown coloring | Disintegration time beginning | after 2 months |
|---|---|---|---|
| Sugar coated tablets of the invention | scarcely observed | 90 sec. | 110 sec. |
| Control | remarkable | 90 sec. | longer than 40 minutes |

EXAMPLE 3

(Sugar Coating)

(1) A sugar coating agent was prepared by the same manner as in Example 1 in the following formulation.

| Hydrogel-like HPC-US*[1] | 6 parts (as HPC-US) |
|---|---|
| Sucrose | 20 parts |
| Water | 74 parts |

(2) Air-spray coated tablets were prepared using the above-mentioned sugar coating agent and the following test was performed.

Preparation of the air-spray coated tablets:

Core tablets of 120 mg/tablet were charged in a coating pan and coated by an ordinary air spray coating until the weight of the tablets became 130 mg/tablet.

Impact test:

The same test as in Example 1 was performed and the following results were obtained.

TABLE 5

Occured number of peeled fragments of the sugar coated layer

| Test sample | Shaking time (min.) | | |
|---|---|---|---|
| | 10 min. | 20 min. | 30 min. |
| Sugar coated tablet of the invention | 0/30 | 1/30 | 4/30 |

In Table 6 are shown the amount of the sugar coating agent and the period of time required for sugar coating.

TABLE 6

| Charged amount | 8,300 tablets |
|---|---|
| Amount of the sugar coating agent | 1,100 g |
| Production time | 5.5 hours |

EXAMPLE 4

(Sugar Coating)

(1) A sugar coating agent was prepared by the same manner as in Example 1 in the following formulation.

| Hydrogel-like HPC-US*[1] | 6 parts (as HPC-US) |
|---|---|
| Sucrose | 20 parts |
| Titanium oxide | 3 parts |
| Water | 71 parts |

(2) Core tablets were coated with an air spray coating as in Example 3 using the sugar coating agent prepared in the above procedure.

Impact test:

The same test as in Example 1 was performed and the following result was obtained.

TABLE 7

Occured number of peeled fragments of the sugar coated layer

| Test sample | Shaking time 30 min. |
|---|---|
| Sugar coated tablet of this invention | 0/30 |

EXAMPLE 5

(Sugar Coating)

(1) A sugar coating agent was prepared by the same manner as in Example 1 in the following formulation.

| Hydrogel-like HPC-US*[1] | 5 parts (as HPC-US) |
|---|---|
| Sucrose | 30 parts |
| Talc | 3 parts |
| Pigment (Yellow No. 5) | 0.002 part |
| Water | 62 parts |

(2) Core tablets were coated with an air spray coating as in Example 3 using the sugar coating agent prepared in the above procedure. The coated tablets showed about the same impact resistance as the coated tablets in Example 3 and changes or degradation of these tablets with the passage of time were observed.

EXAMPLE 6

(Sugar Coating)

(1) A sugar coating agent was prepared by the same manner as in Example 1 in the following formulation.

| Hydrogel-like HPC-US*[1] | 5 parts (as HPC-US) |
|---|---|
| Sucrose | 10 parts |
| Calcium lactate | 10 parts |
| Water | 75 parts |

(2) Sugar coated tablets were prepared by air spray coating as in Example 3 using the sugar coating agent prepared in the above procedure.

Impact test:

The same test as in Example 1 was performed and the following result was obtained.

TABLE 8

| Test sample | Occured number of peeled fragments of the sugar coated layer Shaking time 30 min. |
|---|---|
| Sugar coated tablet of the invention | 0/30 |

EXAMPLE 7

(Film Coat)

(1) A coating agent was prepared by the same manner as in Example 1 in the following formulation.

| Hydrogel-like HPC-US*[1] | 6 parts (as HPC-US) |
|---|---|
| Hydroxypropylmethyl cellulose*[2] | 4 parts |
| Water | 90 parts |

*[2]: TC-5 made by Shinetsu Kagaku Kogyo K. K.

(2) Film coated tablets were prepared using the above-mentioned sugar coating agent and subjected to the following test.

Preparation of the film coated tablets:

Core tablets of 300 mg/tablet were charged in a coating pan and were coated by air spray coating using the coating agent until the weight of the tablet became 310 mg/tablet. In addition, as contrast, film coated tablets were also prepared by the same manner as above using a coating agent prepared using 10 parts of hydroxypropylmethyl cellulose and 90 parts of water.

Moisture absorption test:

The coated tablets were allowed to stand for 15 days at 40° C. and 75% RH. The results are shown in Table 9.

TABLE 9

| Test sample | Weight increase percentage | Thickness increase percentage | Diameter increase percentage |
|---|---|---|---|
| Coated tablet of the invention | 1.0% | 1.1% | 0.4% |
| Control | 1.2% | 2.2% | 0.8% |

EXAMPLE 8

(Film Coat)

(1) A coating agent was prepared by the same manner as in Example 1 in the following formulation.

| Hydrogel-like HPC-US*[1] | 5 parts (as HPC-US) |
|---|---|
| HPC*[3] | 5 parts |
| Water | 90 parts |

*[3]: HPC-SL made by Nippon Soda K. K.

(2) Film coated tablets were prepared as in Example 7 using the sugar coating agent prepared in the above procedure. The product had good appearance and strength.

EXAMPLE 9

(Sugar Coating)

(1) A sugar coating agent and dusting powder were prepared in the following formulations.

| Sugar coating agent: | |
|---|---|
| Hydrogel-like HPC-US*[1] | 1 part (as HPC-US) |
| Sucrose | 59 parts |
| Water | 40 parts |
| Dusting powder: | |
| Dry powder of hydrogel-like HPC-US*[1] | 20 parts |
| Precipitated calcium carbonate | 25 parts |
| Sucrose | 25 parts |
| Talc | 30 parts |

The sugar coating agent was prepared by the same manner as in Example 1.

The dry powder of hydrogel-like HPC-US was prepared by drying and powdering the hydrogel-like HPC-US obtained as in Example 1 using to a spray dry method and the dusting powder was prepared by mixing the dry powder with other powders shown above.

(2) Preparation of sugar coated tablets:

Core tablets of 200 mg/tablet were charged in a coating pan, subcoating was applied thereto using the sugar coating agent for pouring and the dusting powder until the weight of the tablet became 280 mg/tablet, and then the tablets were coated with the above-mentioned sugar coating agent only until the weight of the tablet became 340 mg/tablet. The product had good appearance and strength.

EXAMPLE 10

(Sugar Coating)

(1) A sugar coating agent was prepared in the following formulation.

| Dry powder of hydrogel-like HPC-US*[1] | 3 parts |
|---|---|
| Sucrose | 63 parts |
| Calcium lactate | 4 parts |
| Water | 30 parts |

The dry powder of hydrogel-like HPC-US was prepared by drying and powdering by lyophilization the hydrogel-like HPC-US obtained as in Example 1. The sugar coating agent was prepared by adding thereto water and then dissolving or suspending therein other ingredients.

(2) Sugar coated tablets were prepared by a pouring method as in Example 1 using the above-mentioned sugar coating agent. The product showed almost the same impact resistance as the product in Example 1 and had good appearance.

EXAMPLE 11

(Sugar Coating)

(1) A sugar coating agent was prepared by the same manner as in the following formulation.

| Hydrogel-like HPC-US*[1] | 5 parts (as HPC-US) |
|---|---|
| Sucrose | 10 parts |
| Calcium lactate | 10 parts |

| -continued | |
|---|---|
| Water | 75 parts |

(2) Sugar coated tablets were prepared by means of a fluidized bed coating apparatus using the above-mentioned sugar coating agent and subjected to the following test.

Preparation of the sugar coated tablets:

Core tablets of 120 mg/tablet were charged in a fluidized bed coating apparatus (Uni-Glatt, made by Ookawa Seisakusho K.K.) and coated with the above-mentioned sugar coating agent until the weight of the tablet became 140 mg/tablet. The coating period of time was 3 hours and 45 minutes.

Impact test:

The same test as in Example 1 was performed and the following result was obtained.

TABLE 10

| | Occured number of peeled fragments of the sugar coated layer |
|---|---|
| Test sample | Shaking time 30 min. |
| Sugar coated tablet of the inventon | 0/30 |

EXAMPLE 12

(Sugar Coating)

(1) (a) A sugar coating agent was prepared by the same manner as in Example 1 in the following formulation.

| Hydrogel-like HPC-US*[1] | 2 parts (as HPC-US) |
|---|---|
| Sucrose | 60 parts |
| Calcium lactate | 4 parts |
| Macrogol 20,000 | 2 parts |
| Water | 32 parts. |

(b) Core tablets (150 mg/tab) each containing 25 mg of Cycotiamine which was unstable under warm humidity condition were charged in a coating pan and coated by a conventional pouring method using the above-mentioned sugar coating agent until the weight of the tablet became 210 mg/tab. In addition, at 17 times of coating, the edges of the tablets became round.

(2) (a) A sugar coating agent was prepared as a control in the following formulations.

| Formulation of subcoating solution: | |
|---|---|
| Gelatin | 0.7 part |
| Gum arabic powder | 1.0 part |
| Sucrose | 49.3 parts |
| Precipitated calcium carbonate | 12 parts |
| Talc | 12 parts |
| Water | 25 parts |
| Formulation of simple syrup solution: | |
| Sucrose | 68 parts |
| Water | 32 parts |

(b) Core tablets (150 mg/tablet) containing 25 mg of Cycotiamine as described above were charged in a coating pan and coated by a conventional pouring method using the above-mentioned subcoating solution until the weight of the tablet became 270 mg/tablet. Then, the tablets were further coated by a conventional pouring method using the above-described simple syrup solution until the weight of the tablet became 300 mg/tablet. In addition, at about 40 times of coating by the subcoating solution, the edges of the tablets became round.

Accelerating aging test:

The sugar coated tablets were placed in a bottle which was closed and the tablets were then heated to temperatures of 50° C. and 60° C., while they are placed in a dish under at 40° C., 75 %RH and the tablets were subjected to an accelerating aging test for 3 months. The results obtained are shown in the following table. In addition, 100 sugar coated tablets were used in each test.

TABLE 11

| Test sample | Temperature moisture | Brown coloring | Disintegration time | Number of split tablets |
|---|---|---|---|---|
| Coated tablet of the invention | start | no | 1 min and 45 sec | 0/100 |
| | after 3 months | | | |
| | 50° C. | no | 1 min and 45 sec | 0/100 |
| | 60° C. | no | 2 min and 20 sec | 0/100 |
| | 40° C., 75%RH | no | 1 min and 55 sec | 0/100 |
| Control | start | no | 14 min and 30 sec | 0/100 |
| | after 3 months | | | |
| | 50° C. | remarkable | 48 min and 10 sec | 46/100 |
| | 60° C. | remarkable | more than 60 min | 63/100 |
| | 40° C., 75% RH | remarkable | 32 min and 55 sec | 80/100 |

Also, the amount of the sugar coating agent, the period of time required for the sugar coating, etc., are shown in the following table.

TABLE 12

| | The invention | Control |
|---|---|---|
| Charged amount | 25,000 tablets | 25,000 tablets |
| Amount of sugar coating agent | 2,500 g | 8,000 g |
| Coating times | 30 times | 80 times |
| Produced day | 1.5 days | 4 days |
| Coating amount | 0.4 times the weight of core tablet | 1.0 times the weight of core tablet |

What is claimed is:

1. A composition for coating a solid medicament comprising a hydrogel-like substance of a water-insoluble hydroxypropyl cellulose containing 5-16% by weight of a hydroxypropoxy group.

2. A coating composition according to claim 1 which is in the form of a dry powder.

3. A coating composition for a solid medicament as claimed in claim 1 wherein said coating composition is in a liquid state and contains the hydrogel-like substance or the dry powder thereof in an amount of 0.1-30% by weight as hydroxypropyl cellulose.

4. A coating composition for a solid medicament as claimed in claim 1 or 3 wherein said coating composition is a sugar coating agent and contains the hydrogel-like substance or the dry powder thereof in an amount of 0.1-15% by weight as hydroxypropyl cellulose.

5. A coating composition for a solid medicament as claimed in claim 4 wherein said coating composition contains the hydrogel-like substance or the dry powder thereof in an amount of 1–10% by weight as hydroxypropyl cellulose.

6. A coating composition for a solid medicament as claimed in claim 5 wherein said coating composition contains the hydrogel-like substance or the dry powder thereof in an amount of 1–10% by weight as hydroxypropyl cellulose and calcium lactate in an amount of 1–20% by weight.

7. A coating composition for a solid medicament as claimed in claim 1 or 3 wherein said coating composition is a sugar coating agent for spraying and contains the hydrogel-like substance or the dry powder thereof in an amount of 0.1–10% by weight as hydroxypropyl cellulose.

8. A coating composition for a solid medicament as claimed in claim 7 wherein said sugar coating composition contains the hydrogel-like substance or the dry powder thereof in an amount of 3–7% by weight as hydroxypropyl cellulose.

9. A coating composition for a solid medicament as claimed in claim 8 wherein said sugar coating composition contains the hydrogel-like substance or the dry powder thereof in an amount of 3–7% by weight as hydroxypropyl cellulose and calcium lactate in an amount of 3–15% by weight.

10. A coating composition for a solid medicament as claimed in claim 1 or 3 wherein said coating composition is a film coating agent containing the hydrogel-like substance or the dry powcer thereof in an amount of 1–10% by weight as hydroxypropyl cellulose.

11. A coating composition for a solid medicament as claimed in claim 3 wherein said coating composition is in a powder state containing the dry powder of the hydrogel-like substance.

12. A method of coating solid medicament which comprises coating a solid medicament with the coating composition of claim 1 or claim 2.

13. A solid medicament which is coated with the coating composition of claim 1 or 3.

14. A method of producing a hydrogel-like substance which comprises grinding or kneading 1 part by weight of water-insoluble hydroxypropyl cellulose containing 5–16% by weight of a hydroxypropoxy group in the presence of 5–20 parts of water.

15. A method according to claim 14 wherein 7–13 parts of water is used.

16. A method according to claim 14 wherein the hydrogel-like substance is obtained in the form of a dry powder by drying the final mixture.

17. A hydrogel-like substance of a water-insoluble hydroxypropyl cellulose containing 5–16% by weight of a hydroxypropyl group or the dry powder thereof.

18. The product of the process of claim 14.

19. A composition for coating a solid medicament comprising the product of claim 18 and sugar or a film-forming agent.

20. A compound according to claim 17 having a decomposition starting temperature in the dry powder form of about 15° C. higher than untreated hydroxypropyl cellulose, having the same X-ray diffraction curve at d=4.44 Å but having a full width of half maximum smaller than untreated hydroxypropyl cellulose, having a more amorphous crystalline structure than untreated hydroxypropyl cellulose as observed from a polarizing microphotograph, and having a fused substance-like appearance as observed from electron microphotographs as compared with untreated hydroxypropyl cellulose which has a fibrous crystal.

* * * * *